United States Patent [19]
Ali

[11] Patent Number: 5,830,156
[45] Date of Patent: Nov. 3, 1998

[54] SLIP RESISTANT GUIDEWIRE

[75] Inventor: Mohammed Ali, Shorewood, Wis.

[73] Assignee: Cabot Technology Corporation, Wilmington, Del.

[21] Appl. No.: 843,012

[22] Filed: Apr. 11, 1997

[51] Int. Cl.⁶ ........................................ A61B 5/00
[52] U.S. Cl. ............................ 600/585; 600/434
[58] Field of Search ................... 600/434, 435, 600/585

[56] References Cited

U.S. PATENT DOCUMENTS

| Re. 34,695 | 8/1994 | Mar et al. | 128/772 |
|---|---|---|---|
| 3,547,103 | 12/1970 | Cook | 128/348 |
| 4,548,206 | 10/1985 | Osborne | 128/772 |
| 4,650,472 | 3/1987 | Bates | 604/158 |
| 4,925,445 | 5/1990 | Sakamoto et al. | 604/95 |
| 4,991,602 | 2/1991 | Amplatz et al. | 128/772 |
| 5,167,239 | 12/1992 | Cohen et al. | 600/585 |
| 5,265,622 | 11/1993 | Barbere | 600/585 |
| 5,271,415 | 12/1993 | Foerster et al. | 128/772 |
| 5,341,818 | 8/1994 | Abrams et al. | 600/585 |
| 5,497,782 | 3/1996 | Fugoso | 600/585 |
| 5,636,642 | 6/1997 | Palermo | 600/585 |

OTHER PUBLICATIONS

Excerpt from Circon Corporation "1997 Complete Product Catalog", Copyright 1996, pp. U–92–U–95 (SURLOK™ Products).

*Primary Examiner*—Max Hindenburg
*Assistant Examiner*—Charles Marmor, II
*Attorney, Agent, or Firm*—Austin R. Miller

[57] ABSTRACT

A guidewire is provided for partial insertion into a surgical patient. One embodiment of the guidewire is adapted for advancement to a desired position within the patient and for resisting slippage from the desired position. The guidewire includes a body portion, at least one flexible end, and means for resisting slippage of the guidewire into or out from the desired position.

14 Claims, 5 Drawing Sheets

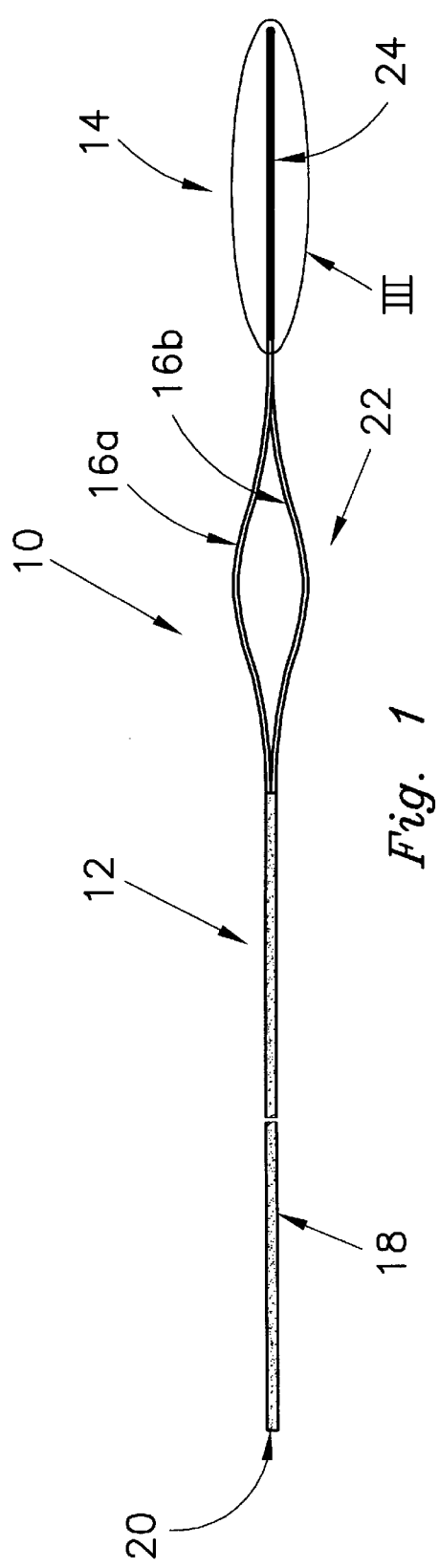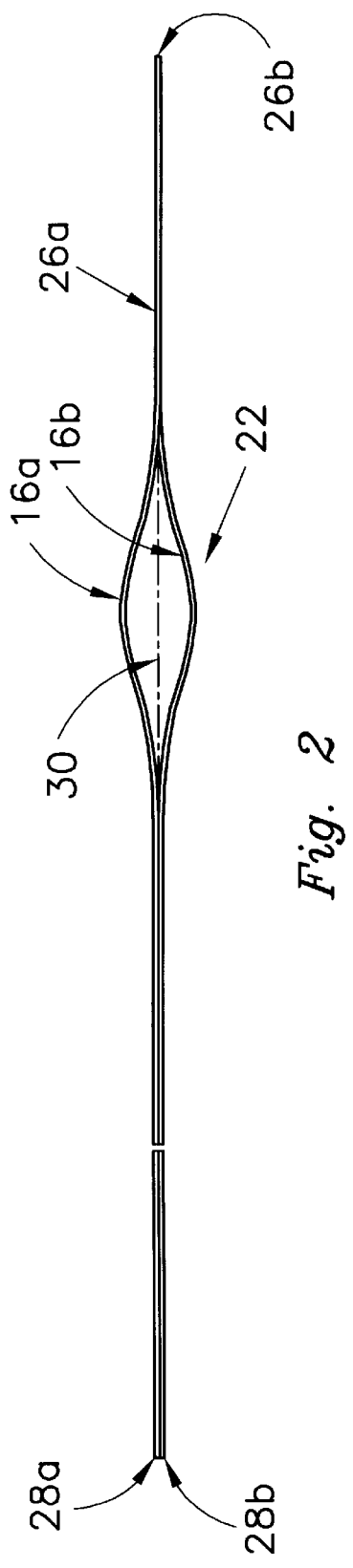

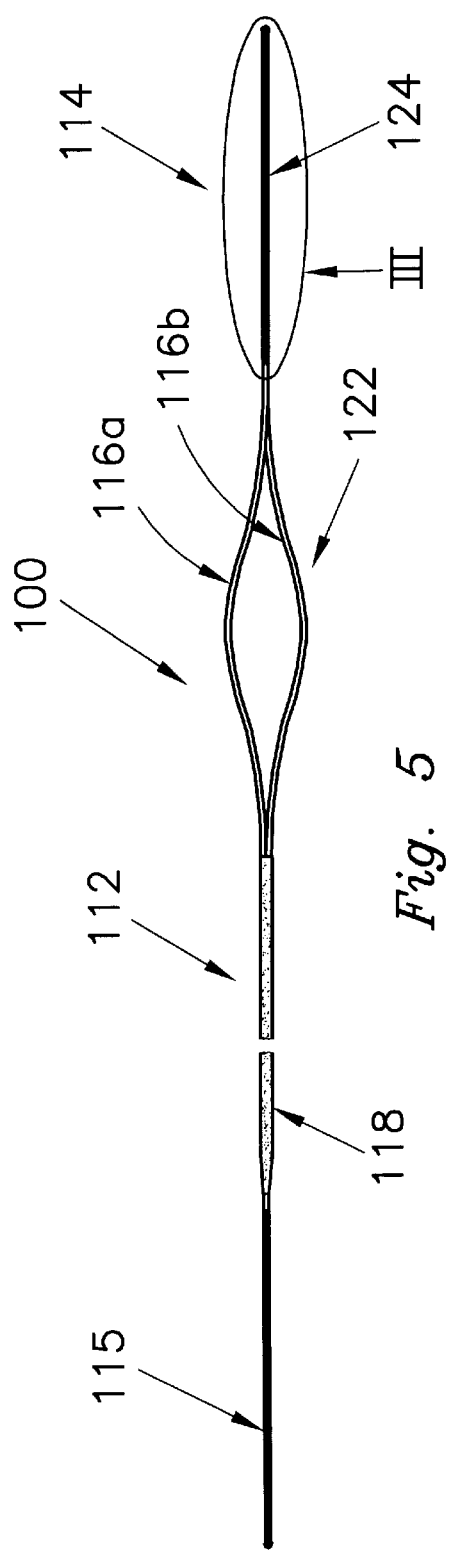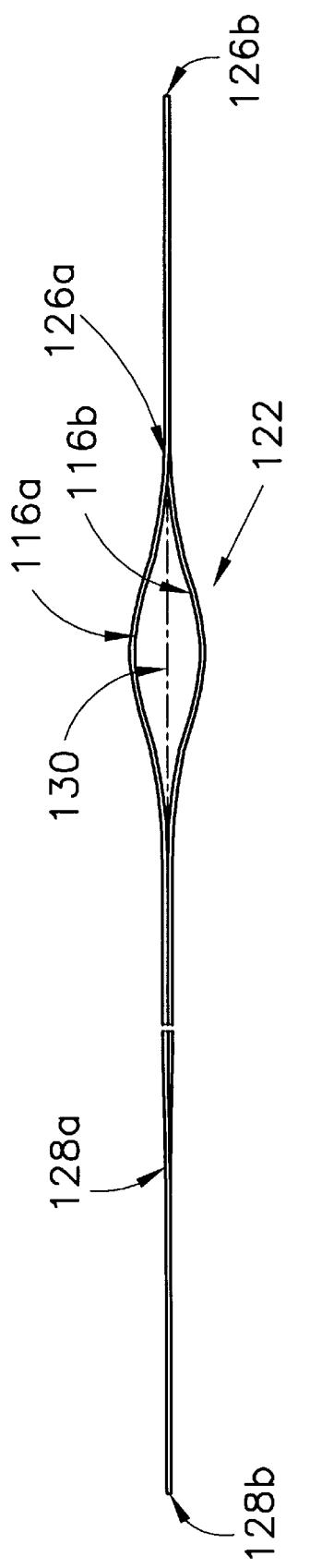

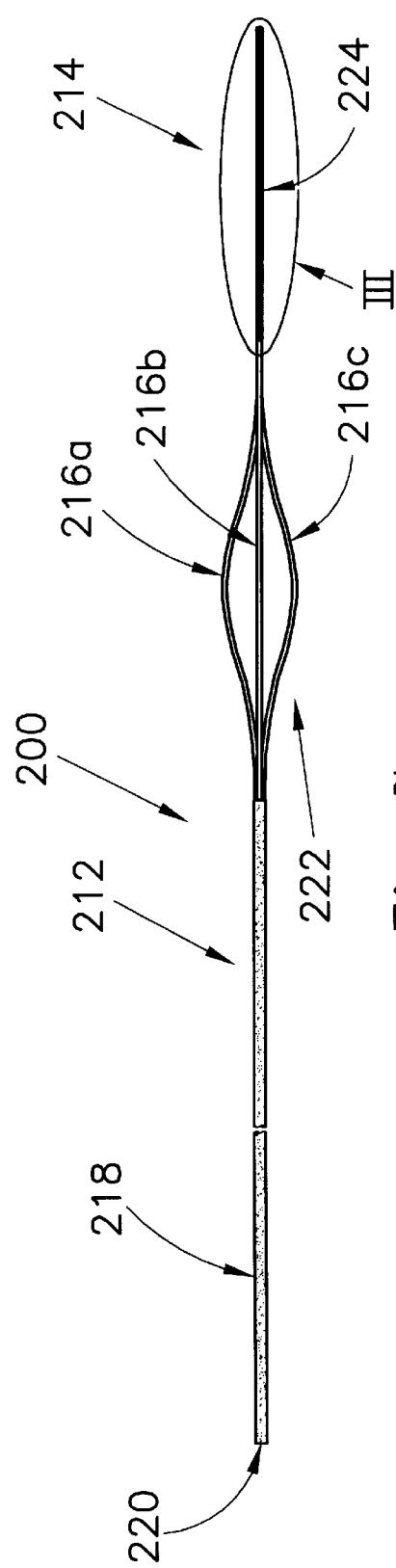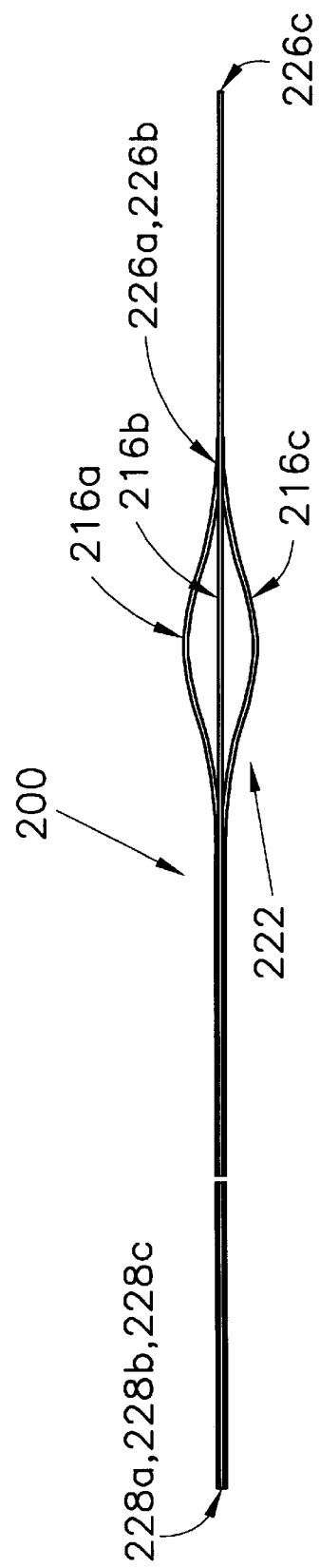

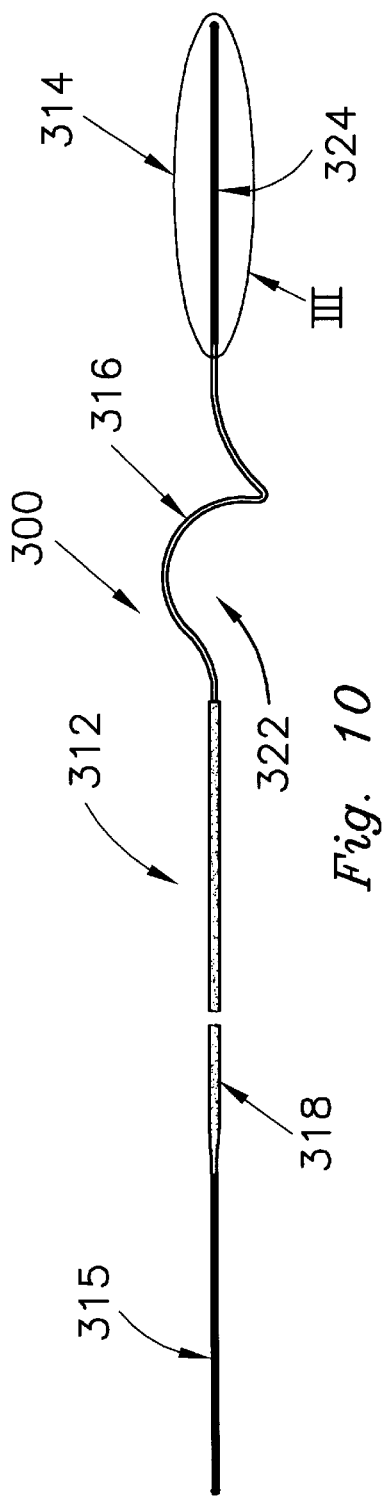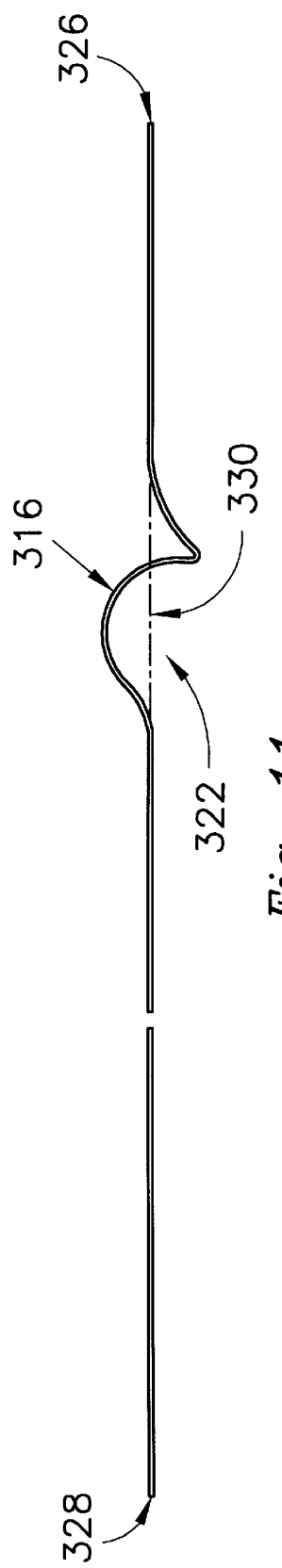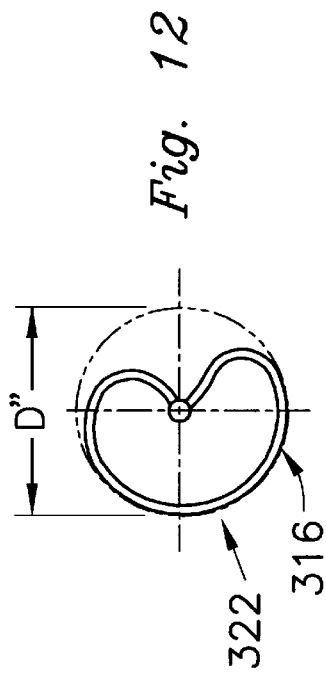

SLIP RESISTANT GUIDEWIRE

FIELD OF THE INVENTION

This invention relates to a medical guidewire for insertion into the blood vessels, trachea, urinary tract, digestive tract, or other body cavities or the like. Particularly, it relates to a guidewire adapted for insertion into a patient and for resisting slippage after insertion to a desired location.

BACKGROUND OF THE INVENTION

Guidewires are increasingly popular for use during medical procedures in order to provide access to inner passages of the body.

Guidewires are often used to position catheters into body passages for the introduction or removal of fluid. For example, percutaneous catheterization of blood vessels uses conventional catheterization techniques, such as the one developed by Dr. Seldinger, for blood sampling, blood pressure monitoring or for the administration of drugs and fluids. The Seldinger technique frequently uses an introduction needle to enter a blood vessel with minimal trauma. To insert the catheter, a guidewire is inserted through the straight bore of the needle, the needle is withdrawn, the catheter is inserted by sliding it over the guidewire, and the guidewire is withdrawn.

Various guidewires have been proposed for percutaneous catheterization. For example, Bates U.S. Pat. No. 4,650,472 proposes an improved Seldinger technique for inserting catheters using a smaller introduction needle. Amplatz et al U.S. Pat. No. 4,991,602 proposes another guidewire for use during percutaneous catheterization. Other guidewires for percutaneous catheterization are proposed by Cook U.S. Pat. No. 3,547,103; Osborne U.S. Pat. No. 4,548,206; and Sakamoto et al U.S. Pat. No. 4,925,445.

Another conventional use for guidewires includes balloon angioplasty procedures, during which a guidewire is maneuvered to an acute restriction in a patient's cardiovasculature, a balloon is inflated to open the restriction, and the balloon is removed with the guidewire. Angioplasty guidewires are proposed by Foerster et al U.S. Pat. No. 5,271,415, and Mar et al U.S. Reissue No. 34,695.

Endoscopes have become increasingly popular for visualization in a wide variety of procedures. The indications for endoscopy continue to expand with increasing experience. Ureteroscopy, for example, has now taken a significant role in the therapy of upper urinary calculi, the diagnosis and treatment of vascular lesions and even for the treatment of urethral neoplasms. Other uses for ureteroscopes have also been proposed, as described in the book "Techniques with the Flexible Ureteroscope," by Demetrius H. Bagley, M.D.

Guidewires are frequently used for the initial insertion of a flexible endoscope. In one technique, a flexible endoscope is introduced over a guidewire by first positioning the guidewire into a body passage cystoscopically. The proximal end of the guidewire is then placed retrograde (proximal-end first) through a working channel of the endoscope. After the proximal end of the guidewire is passed through the working channel, it is retrieved as it exits the working channel port on the endoscope handle. The endoscope is subsequently advanced over the guidewire and into the body passage.

Guidewires are also used for the guidance of stents as they are positioned within a patient. In such a procedure, the guidewire is first positioned at a desired location within the patient. The stent is subsequently inserted into the patient over the guidewire.

In many modern procedures during which guidewires are utilized, it can be important to accurately position the guidewire in the patient and to retain the guidewire at that position until a desired task is accomplished. Nevertheless, guidewires are preferably designed and manufactured to facilitate insertion into the patient without undue resistance, and guidewires can tend to slip, migrate or otherwise move with respect to the patient so that the tip of the guidewire moves away from the desired position selected by the surgeon. Such a tendency requires additional attention and perhaps repositioning of the guidewire.

OBJECTS OF THE INVENTION

It is an object of this invention to provide an improved guidewire to overcome disadvantages of the prior art.

It is another object of this invention to provide an improved guidewire adapted for insertion into a patient and for resisting slippage after it has been inserted into the patient.

Other objects will be apparent in view of the following description, the drawings, and the appended claims.

SUMMARY OF THE INVENTION

In a preferred embodiment, a guidewire is provided for partial insertion into a patient wherein the guidewire is adapted for advancement to a desired position within the patient as well as for resisting slippage from that desired position. Such an embodiment includes a body portion that is formed from one or more wires which run along the length of the body portion. A jacket, preferably formed from a polymer, surrounds at least a portion of the wire or wires in the body portion. The guidewire also includes a distal portion adapted for insertion into the patient. The distal portion includes a tip having a degree of flexibility greater than that of the body portion so that it can easily conform to contours within the patient. The guidewire also includes a means for resisting slippage of the guidewire into or out from the desired position within the surgical patient. Such means is positioned along the body portion of the guidewire and is located between the tip of the guidewire and the jacket, in one embodiment.

BRIEF DESCRIPTION OF THE DRAWINGS

FIG. 1 is a side view of an embodiment of a guidewire according to this invention.

FIG. 2 is a side view of a component of the guidewire shown in FIG. 1.

FIG. 5 is a side view of another embodiment of a guidewire according to this invention.

FIG. 6 is a side view of a component of the guidewire shown in FIG. 5.

FIG. 7 is a side view of yet another embodiment of a guidewire according to this invention.

FIG. 8 is a side view of a component of the guidewire shown in FIG. 7.

FIG. 10 is a side view of still another embodiment of a guidewire according to this invention.

FIG. 11 is a side view of a component of the guidewire shown in FIG. 10.

FIG. 12 is an end view of the guidewire shown in FIG. 10.

DETAILED DESCRIPTION OF THE INVENTION

Figure 3:
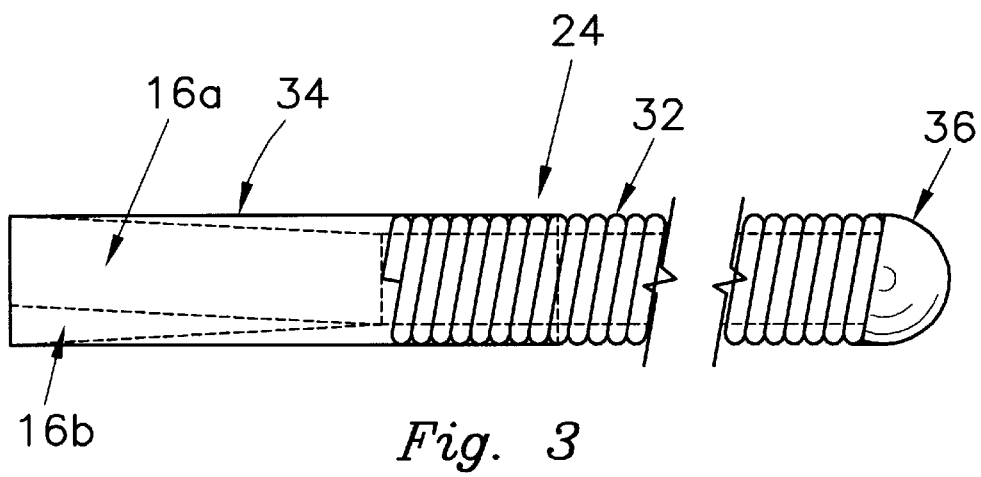
FIG. 3 is a side view of a detail of the guidewire shown in FIG. 1, as defined in FIG. 1.

It will be appreciated that the following description is intended to refer to specific aspects of the invention selected for illustration in the drawings and is not intended to define or limit the invention as set forth in the appended claims.

Turning to FIG. 1, an embodiment of a guidewire according to this invention is shown, generally designated with the numeral "10". Guidewire 10 is adapted for insertion into a body passage of a surgical patient. It is also adapted to resist against slippage of the guidewire within the patient's body passage after it has been inserted.

In this embodiment, slip resistant guidewire 10 includes an elongated body portion 12 which is connected to an flexible distal tip portion 14. Details of tip portion 14 and a coil spring 24 positioned at tip portion 14 will be described later with reference to FIG. 3. Body portion 12 of guidewire 10 is formed in part by a pair of wires 16a and 16b. As will be described, wires 16a and 16b extend all the way from tip portion 14 to a position adjacent to proximal end 20 of guidewire 10. A so-called "retainer" 22 is formed adjacent to tip portion 14. Retainer 22 will be described in further detail with reference to FIG. 2.

Wires 16a and 16b are preferably metallic in construction. Most preferably, they are formed from a nickel-titanium alloy such as the alloy available under the name NITINOL. Although wires 16a and 16b can be provided with a variety of shapes and sizes, and may differ in shape and size from one another, wires 16a and 16b are most preferably of circular cross-sectional shape. Although a wide variety of dimensions can be used, wires 16a and 16b are preferably of a small diameter. In one preferred embodiment, two NITINOL wires having a diameter of about 0.015-inch are used.

A coating or jacket 18 is positioned over a portion of the length of wires 16a and 16b. Jacket 18 is preferably formed from a polymeric or plastic material such as tetrafluoroethylene (or TFE), polyurethane, polyethylene, silicone or other materials. If jacket 18 is formed from TFE, it is preferably formed by placing TFE heat-shrink tubing over wires 16a and 16b and then heating the tubing so that it shrinks into close contact with the wires. At proximal end 20, such tubing can be formed together to encapsulate the ends of the wires. If polyurethane or polyethylene is used for jacket 18, it is preferably co-extruded with the wires 16a and 16b in order to provide an encapsulating jacket. Also, if polyurethane or polyethylene are used, an additional coating is optionally applied over the polyurethane or polyethylene jacket in order to reduce the coefficient of friction of the jacket's surface so that it can be easily inserted into a surgical patient.

Referring now to FIG. 2, a core assembly of guidewire 10 is illustrated without jacket 18 or coil spring 24. A centerline 30 is illustrated in FIG. 2 in order to emphasize the preferred curvature of wires 16a and 16b at the location of retainer 22. If the wires are formed from NITINOL as in the preferred embodiment, such curvature is provided by individually forming a curvature in otherwise straight wires 16a and 16b in an oven at a predetermined temperature and for a predetermined duration known in the art. Alternatively, wires 16a and 16b can be formed in a common jig at the same time, if desired. As illustrated in FIG. 2, wire 16a extends from a distal end 26a along the entire length of body portion 12 to a proximal end 28a. Wire 16a does not extend the full length of guidewire 10 for reasons which will be made clear with the description of tip portion 14 and coil spring 24 as described with reference to FIG. 3. However, wire 16b does extend substantially the full length of guidewire 10 from a distal end 26b to a proximal end 28b.

Referring to FIGS. 1 and 2 together, wires 16a and 16b are formed into a so-called "retainer" which is designated with the numeral "22". For this preferred embodiment, the term "retainer" is intended to refer to one or more wires that is or are positioned with a portion away from the longitudinal axis or centerline of the guidewire. If more than one wire is used, then they can be positioned adjacent to one another at the ends of the retainer but radially spaced from one another toward the center of the retainer. As will be described later in connection with the operation of guidewire 10, retainer 22 has sufficient flexibility in the radial direction so that wires 16a and 16b are capable of collapsing toward one another so that guidewire 10 can be advanced into or out from a passage or so that a medical device (such as a stent, for example) or instrument (such as a ureteroscope, for example) can be passed over guidewire 10. At the same time, the resilience of wires 16a and 16b at the location of retainer 22 is sufficient to generate a radially outward force capable, when inserted into a desired position in a patient, of resisting slippage of guidewire 10 with respect to the patient's body passage away from the desired position. Although many possible dimensions are contemplated, a preferred guidewire 10 is optionally provided with a space in the range of about one-quarter inch between wires 16a and 16b at the central region of retainer 22.

In addition to the benefits of retainer 22 described above, a retainer formed from more than one wire also provides an additional benefit. Circon Surgitek of Racine, Wis. offers stone retrieval devices under the trademark SURLOK (Model Nos. 57000XX and 57100XX, for example). Such retrieval devices include a handle, a sheath, and a mechanism for advancing and retracting wire "baskets". Although guidewire 10 is very different from such retrieval devices in that it is adapted for insertion and retention in the patient so that devices or instruments can be guided thereover (which is impossible using stone retrieval devices), retainer 22 can also be adapted to capture and remove loose matter from a patient as the guidewire is withdrawn.

Referring now to FIG. 3, a detail of tip portion 14 of guidewire 10 is illustrated, including preferred aspects of coil spring 24 (detail "III" in claim 1). Tip portion 14 is provided with a coil wire 32 that is helically wrapped adjacent to the distal end 26a of wire 16a and extends over wire 16b to its distal end 26b. In one embodiment, coil wire 32 is formed from a stainless steel wire having a diameter of about 0.004-inch, although other materials and dimensions are of course contemplated. Coil wire 32 extends from a wire connector 34 that provides a connection point for wires 16a, 16b and an end of coil wire 32. As shown in FIG. 3, wires 16a and 16b extend into wire connector 34 from the left-hand side of the figure. At the opposite end of coil spring 24, a solder ball cap 36 is provided to terminate coil wire 32 and connect coil wire 32 to distal end 26b of wire 16b. Most preferably, solder ball cap 36 is smooth and rounded to facilitate atraumatic insertion into the body passage of a patient. Although its length can vary widely depending on design preference, coil spring 24 preferably has a length of about one inch. Other examples of coil constructions are proposed in Cook U.S. Pat. No. 3,547,103, and Mar et al U.S. Reissue No. 34,695, both of which are incorporated herein by reference.

Figure 4:
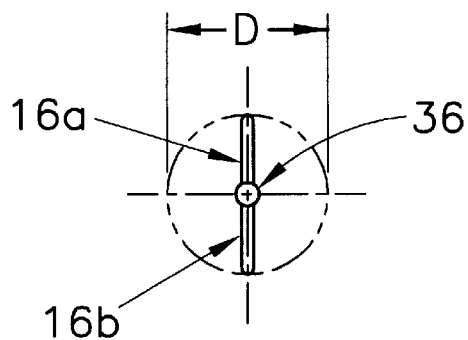
FIG. 4 is an end view of the guidewire shown in FIG. 1.

Referring now to the end view illustrated in FIG. 4, it can be seen that wires 16a and 16b expand outwardly from one another in a central portion of retainer 22 at about 180° from one another. The wires 16a and 16b are within a diameter "D". As mentioned previously, a preferred diameter D is about one-quarter inch but can vary depending on the intended application for the guidewire as well as manufacturing considerations and material selections.

FIG. 5 illustrates another embodiment of a guidewire according to this invention, generally designated by the numeral "100". Guidewire 100 is similar to guidewire 10 in almost every regard in that it includes a body portion 112, a flexible distal tip portion 114, wires 116a and 116b, a jacket 118, a retainer 122, and a coil spring 124. However, guidewire 100 differs from guidewire 10 in that it also includes a flexible proximal tip portion 115 at its proximal end. Proximal tip portion 115 is optionally identical in construction to the tip portion 14 as described with reference to FIG. 3 above.

Although tip portions 14, 114 and 115 are illustrated as substantially straight tips, they are optionally provided with a curved or bent configuration, depending upon their intended uses. Alternatively, a bent or curved tip can be provided at one end with a straight tip at the other end. The benefit of providing a flexible tip (such as tips 114 and 115) at both ends of the guidewire is one of versatility. For procedures during which guidewire retention is important or desirable, the flexible tip adjacent to the retainer is inserted into the patient. For other procedures, the flexible tip at the end opposite the retainer is inserted. Accordingly, the guidewire is versatile for all guidewire-related procedures.

Referring now to FIG. 6, the core construction of guidewire 100 is illustrated. As shown, a retainer 122 is formed in wires 116a and 116b so that the wires in that portion are spaced away from each other and away from centerline 130. Wire 116a extends from a distal end 126a to a proximal end 128a. Wire 116a does not extend to the ends of guidewire 100 due to the formation of the flexible tips 114 and 115. In contrast, wire 116b extends substantially the full length of the guidewire 100, from a distal end 126b to a proximal end 128b.

Figure 9:
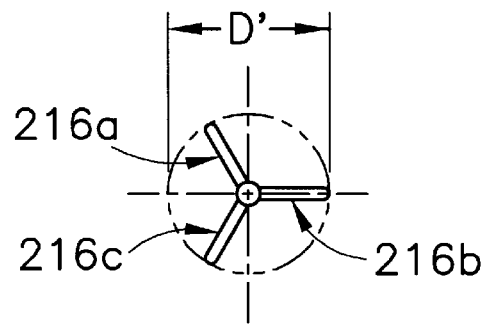
FIG. 9 is an end view of the guidewire shown in FIG. 7.

Referring now to FIG. 7, yet another embodiment of a guidewire according to this invention is illustrated. This guidewire is generally designated by the numeral "200" and differs from the previous embodiments in that it includes three wires in its body. As shown in FIG. 7, guidewire 200 includes a body portion 212 terminating at a flexible distal tip 214. Body portion 212 is formed in part by three wires 216a, 216b and 216c. As with the previous embodiments, a portion of the wires are covered by a jacket 218 that extends to the proximal end 220 of guidewire 200. Wires 216a, 216b and 216c together form a retainer 222, further details of which are illustrated in FIG. 9. The flexible distal tip 214, as well as coil spring 224, are essentially the same in construction as that shown in FIG. 3.

FIG. 8 illustrates the core construction of guidewire 200. Each of wires 216a, 216b and 216c terminate at adjacent proximal ends 228a, 228b and 228c, respectively. Wire 216c extends over substantially the entire length of guidewire 200 from a proximal end 228c to a distal end 226c. In contrast, wires 216a and 216b terminate at distal ends 226a and 226b, respectively, which are adjacent one another. The three-wire retainer of guidewire 200 operates in a similar manner to the two-wire retainer of guidewires 10 and 100.

Referring now to FIG. 9, it can be seen that wires 216a, 216b and 216c extend outwardly from the central axis of guidewire 200 to define an outermost diameter D'. The wires are preferably separated from one another by about 120° so that they are evenly disposed in the radial direction. Again, although other dimensions are surely contemplated, diameter D' is preferably about one-quarter inch.

Because three wires are used to form guidewire 200, it is preferred that each of the wires is provided with a smaller diameter than those used in guidewires 10 and 100. In fact, a diameter of about 0.010-inch is most preferred for this embodiment. By using such smaller-diameter wires, the overall outer dimensions of jacket 218 and coil spring 224 can remain the same as for the two-wire embodiments.

Although not shown, guidewire 200 is optionally provided with flexible tip portions at both ends. In other words, guidewire 200 is optionally provided with a proximal tip portion similar in nature and construction to flexible distal tip portion 214 as described in FIG. 3.

Many modifications to the illustrated embodiments are contemplated. For example, the construction of the tip portions can be modified from the coil construction illustrated in the drawings and tapered tips and other flexible constructions are contemplated. Examples of various compositions for a solid core and for alternative coatings or tips are described in Sakamoto et al U.S. Pat. No. 4,925,445 and Mar et al U.S. Reissue No. 34,695, incorporated herein by reference.

Also, although the guidewires illustrated in the drawings described thus far include two or more wires, it is also contemplated that a single-wire guidewire can be provided according to this invention. Referring for example to FIG. 10, a guidewire 300 is shown. It is similar to guidewires 10 and 100 except that it includes only a single wire 316. Guidewire 300 includes a body portion 312, flexible tip portions 314 and 315, a jacket 318, and a retainer 322. As shown in the end view of FIG. 12, wire 316 is formed into a shape having a portion that extends away from the centerline or longitudinal axis 330 of the body portion. The retainer 322 defines a diameter D" that can vary according to the specific procedure for which the guidewire is manufactured. Referring to FIG. 11, wire 316 extends from a distal end 326 to a proximal end 328, and runs substantially the entire length of guidewire 300. As with retainers 22, 122 and 222, retainer 322 has sufficient flexibility to collapse for insertion into a body passage or other device or instrument. It also has sufficient radial force to resist slippage of guidewire 300 from a desired position in a body passage. Although retainer 322 has a three-dimensional configuration, any helical, convoluted, curved, or otherwise oriented configuration, whether two- or three-dimensional, is contemplated as well. Also, although jacket 318 terminates adjacent to retainer 322 as shown in FIG. 10, it optionally extends over retainer 322 or even encapsulates the entire surface of guidewire 300, if desired. Guidewire 300 is especially well adapted for such encapsulation because it includes only one wire, but multiple-wire guidewires such as guidewires 10, 100 and 200 can also be completely encapsulated or have a jacket extending over the retainer.

Although preferred embodiments of a guidewire according to this invention are illustrated in the drawings, this invention is not limited to the embodiments shown. Various modifications are contemplated without departing from the spirit or scope of this invention as it is defined in the appended claims. Also, the drawings are not to scale and various dimensions are contemplated.

What is claimed is:

1. A guidewire adapted for partial insertion into a body passage of a surgical patient and adapted for contact with an interior surface of said body passage, a portion of said guidewire being adapted for advancement to a desired position within said body passage and for resisting unintended slippage of said guidewire from said desired position, said guidewire comprising:

a body comprising at least one wire running along the length of said body;

a tip portion connected to said body, said tip portion having a degree of flexibility greater than that of said body; and means for resisting unintended slippage of said guidewire away from said desired position within said body passage without seperate control, said means being positioned along said body at a location adjacent to said tip portion, said means having sufficient flexibility to at least partially collapse for insertion into said body passage, and having sufficient radial force to resist said unintended slippage, upon contact between said means and said interior surface of said body passage.

2. The guidewire defined in claim 1, wherein said wire is metallic.

3. The guidewire defined in claim 2, wherein said wire is formed from an alloy of titanium and nickel.

4. The guidewire defined in claim 1, wherein said body further comprises a jacket surrounding at least a lengthwise portion of said wire, said jacket being formed from a biocompatible material.

5. The guidewire defined in claim 1, wherein said tip portion has a coiled construction formed in a predetermined configuration and adapted to be flexed and returned to said predetermined configuration.

6. The guidewire defined in claim 1, wherein said means comprises a retainer formed from two or more wires, said wires being radially separated from one another at a central portion of said retainer, wherein said retainer has sufficient resilience to collapse radially for insertion of said guidewire through a passageway, and wherein said retainer has sufficient radial strength to resist slippage of said guidewire from said desired position within a surgical patient.

7. A guidewire adapted for partial insertion into a body passage of a surgical patient and adapted for contact with an interior surface of said body passage, a portion of said guidewire being adapted for advancement to a desired position within said body passage and for resisting unintended slippage of said guidewire from said desired position, said guidewire comprising:

a body having a distal end portion and a longitudinal axis;

a retainer formed along said distal end portion of said body and positioned for contact with said interior surface of said body passage, said retainer comprising at least one wire having a portion that is radially separated from said longitudinal axis of said body between end portions of said retainer; and a tip portion connected adjacent to said distal end portion of said body, said tip portion having a degree of flexibility greater than that of said body;

wherein said retainer has sufficient flexibility to at least partially collapse for insertion into said body passage upon said contact with said interior surface of said body passage; and wherein said retainer has sufficient radial force to resist unintended slippage from a desired position in said body passage upon said contact.

8. The guidewire defined in claim 7, wherein said wire extends along substantially the entire length of said body.

9. The guidewire defined in claim 7, wherein said retainer is formed from two or more wires and said wires are radially separated from one another in substantially opposite directions to form said retainer.

10. A guidewire for partial insertion into a surgical patient, a portion of said guidewire being adapted for advancement to a desired position within the body passage of a surgical patient and for resisting unintended slippage of said guidewire from said desired position, said guidewire comprising:

a body portion;

a retainer defined along a distal end portion of said body portion, said retainer having a proximal end portion and a distal end portion spaced from said proximal end portion, wherein said retainer comprises at least two wires extending from said proximal end portion to said distal end portion, and wherein said retainer is formed by configuring said wires so that they are radially separated from one another at a location between said proximal end portion of said retainer and said distal end portion of said retainer and converge toward one another adjacent to said proximal and distal end portions of said retainer; and wherein said retainer has sufficient resilience to at least partially collapse for insertion of said guidewire into said body passage, and wherein said retainer has sufficient radial strength to resist unintended slippage of said guidewire from said desired position within said body passage.

11. The guidewire defined in claim 10, wherein a proximal tip portion is connected adjacent to a proximal end of said body portion, wherein said proximal tip portion has a degree of flexibility greater than that of said body portion.

12. The guidewire defined in claim 10, said guidewire further comprising a tip portion connected adjacent to said distal end portion of said retainer, said tip portion having a degree of flexibility greater than that of said body portion.

13. The guidewire defined in claim 10, said body portion comprising at least two wires running along the length of said body portion.

14. The guidewire defined in claim 10, further comprising a jacket surrounding a lengthwise portion of said wires.

* * * * *